United States Patent [19]

Hu

[11] Patent Number: 5,400,255
[45] Date of Patent: Mar. 21, 1995

[54] RECONSTRUCTION OF IMAGES FROM CONE BEAM DATA

[75] Inventor: Hui Hu, Waukesha, Wis.

[73] Assignee: General Electric Company, Milwaukee, Wis.

[21] Appl. No.: 194,894

[22] Filed: Feb. 14, 1994

[51] Int. Cl.⁶ .................. G06F 15/42; G06K 9/00
[52] U.S. Cl. .................. 364/413.19; 364/413.13; 364/413.14; 364/413.16; 364/413.20; 364/413.21; 364/413.15; 382/6; 378/901
[58] Field of Search .............. 364/413.13, 413.14, 364/413.15, 413.16, 413.17, 413.19, 413.21, 413.24; 382/6; 250/363.01, 363.02, 363.03, 363.04, 363.1; 345/149; 395/125, 126, 127; 378/901; 128/653.1, 659, 664

[56] References Cited

U.S. PATENT DOCUMENTS

| | | | |
|---|---|---|---|
| 4,057,727 | 11/1977 | Muehllehner | 250/363 S |
| 4,752,691 | 6/1988 | Hawman | 250/363.1 |
| 5,170,439 | 12/1992 | Zeng et al. | 382/6 |
| 5,257,183 | 11/1993 | Tam | 364/413.19 |
| 5,270,926 | 12/1993 | Tam | 364/413.19 |
| 5,291,402 | 3/1994 | Pfoh | 364/413.14 |

OTHER PUBLICATIONS

Cao, et al. ("Improved Image Quality for Asymmetric Double-focal Cone-Beam Spect", *IEEE Trans. on Nuclear Sci.)*, vol. 40, No. 4, Aug. 1993, pp. 1145–1148.

Wang, et al. ("A General Cone-Beam Reconstruction Algorithm", *IEEE Transactions on Medical Imaging)*, vol. 12, No. 3, Sep. 1993, pp. 486–496.

Practical Cone-Beam Algorithm, 1984 Optical Society of America, L. A. Feldkamp, et al.

Mathematical Framework of Cone Beam 3D Reconstruction via the First Driivative of the Radon Transform, Pierre Grangeat, 1990.

Cone Beam Convultion Formula, Bruce D. Smith.

An Inversion Formula for Cone-Beam Reconstruction, Heango K. Tuy, Jun., 1983.

Quantitives Cone Beam Reconstruction, Hui, Hu, et al.

*Primary Examiner*—Gail O. Hayes
*Assistant Examiner*—Joseph Thomas
*Attorney, Agent, or Firm*—Quarles & Brady

[57] ABSTRACT

A computed tomography x-ray imaging system acquires a three-dimensional array of x-ray attenuation values using a cone beam x-ray source [(13)] and a curved two-dimensional array of detector elements [(16)]. Two-dimensional image slices [(55)] are reconstructed using a filtered back projection method, and corrections are made to the images to account for inaccuracies in the reconstruction method and for incomplete data due to the cone beam geometry.

5 Claims, 4 Drawing Sheets

RECONSTRUCTION OF IMAGES FROM CONE BEAM DATA

BACKGROUND OF THE INVENTION

The present invention relates to computed tomography (CT) imaging apparatus; and more particularly, to reconstruction of images from three-dimensional data acquired with x-ray CT or SPECT scanners.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a cathode ray tube display.

In a 3D scan the x-ray beam diverges to form a cone beam that passes through the object and impinges on a two-dimensional array of detector elements. Each view is thus a 2D array of x-ray attenuation measurements and the complete scan produces a 3D array of attenuation measurements. Either of two methods are commonly used to reconstruct a set of images from the acquired 3D array of cone beam attenuation measurements. The first method described by L. A. Feldkamp et al in "Practical Cone-Beam Algorithm", *J. Opt. Soc. Am.*, A/Vol. 1, No. 6/Jun. 1984 is a convolution backprojection method which operates directly on the line integrals of the actual attenuation measurements. The method can be implemented easily and accurately with current hardware and it is a good reconstruction for images at the center or "midplane", of the cone beam. The Feldkamp method employs the conventional convolution - back projection form, but this is an approximation that becomes less accurate at larger cone beam angles. The second method proposed by Pierre Grangeat in "Mathematical Framework of Cone Beam 3D Reconstruction Via the First Derivative of the Radon Transform", *Mathematical Methods In Tomography*, Herman, Louis, Natterer (eds.), Lecture notes in Mathematics, No. 1497, pp. 66–97, Spring Verlag, 1991, provides an accurate solution to the image reconstruction task based on a fundamental relationship between the derivative of the cone beam plane integral to the derivative of the parallel beam plane integral. While this method is theoretically accurate, it requires mathematical operations that can only be solved using finite numerical calculations that are approximations. The errors introduced by the implementation of the Grangeat method can be greater than Feldkamp and these errors are not correlated with cone beam angle.

SUMMARY OF THE INVENTION

The present invention relates to a computer tomography system which produces a three-dimensional array of data from which a set of 2D image slices can be reconstructed. More specifically, the system includes a 2D array of detector elements for receiving photons in a cone beam produced by a source while the two are rotated about a central axis to acquire data at a series of views, an image reconstructor which employs filtered back projection of the acquired cone beam data to produce image data $f_{m0}(r)$; means for calculating a correction image $f_{m1}(r)$ from the acquired cone beam data by filtering and backprojecting; and means for combining the correction image data $f_{m1}(r)$ with the back projection image data $f_{m0}(r)$ to produce an image slice.

A general object of the invention is to accurately reconstruct image slices from 3D cone beam data. A filtered back projection method is employed to accurately and efficiently produce the main part of the reconstruction. A second set of image data is also produced by summing the acquired cone beam data along each of its rows, filtering and weighting this summed data and back projecting it. The resulting correction image $f_{m1}(r)$ is combined with the back projection image $f_{m0}(r)$ to produce the more accurate image slice.

DESCRIPTION OF THE PREFERRED EMBODIMENT

Figure 1:
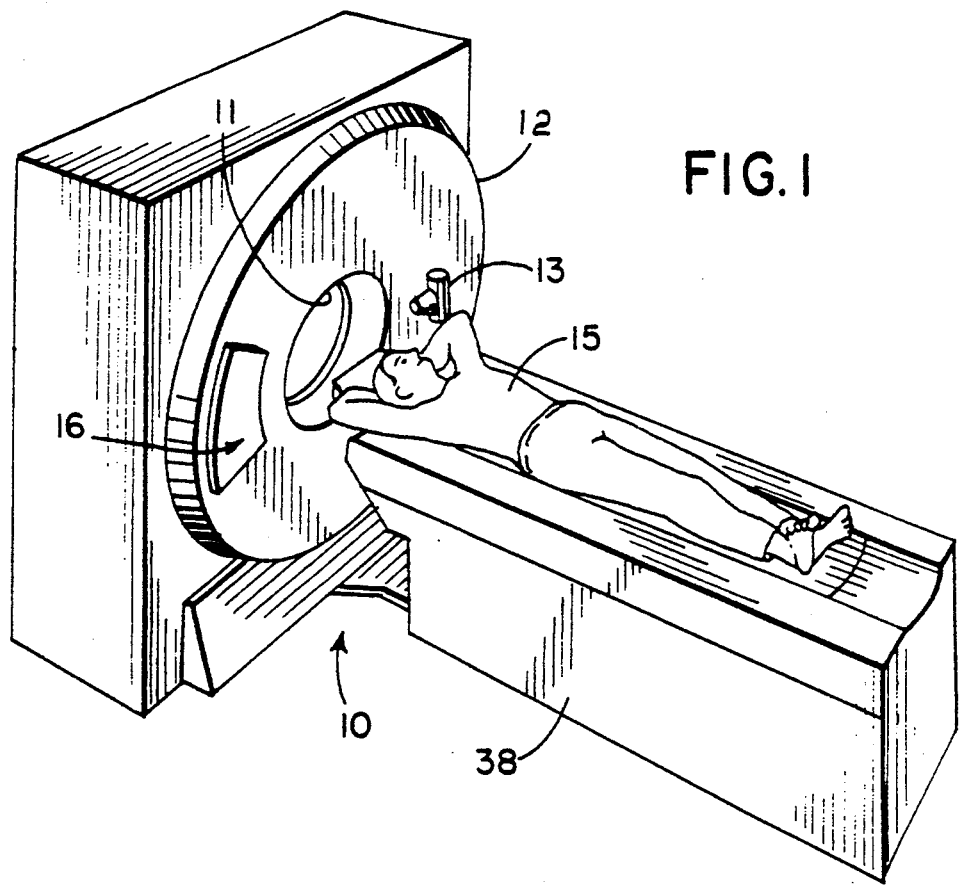
FIG. 1 is a pictorial view of a CT imaging system in which the present invention may be employed.
Figure 2:
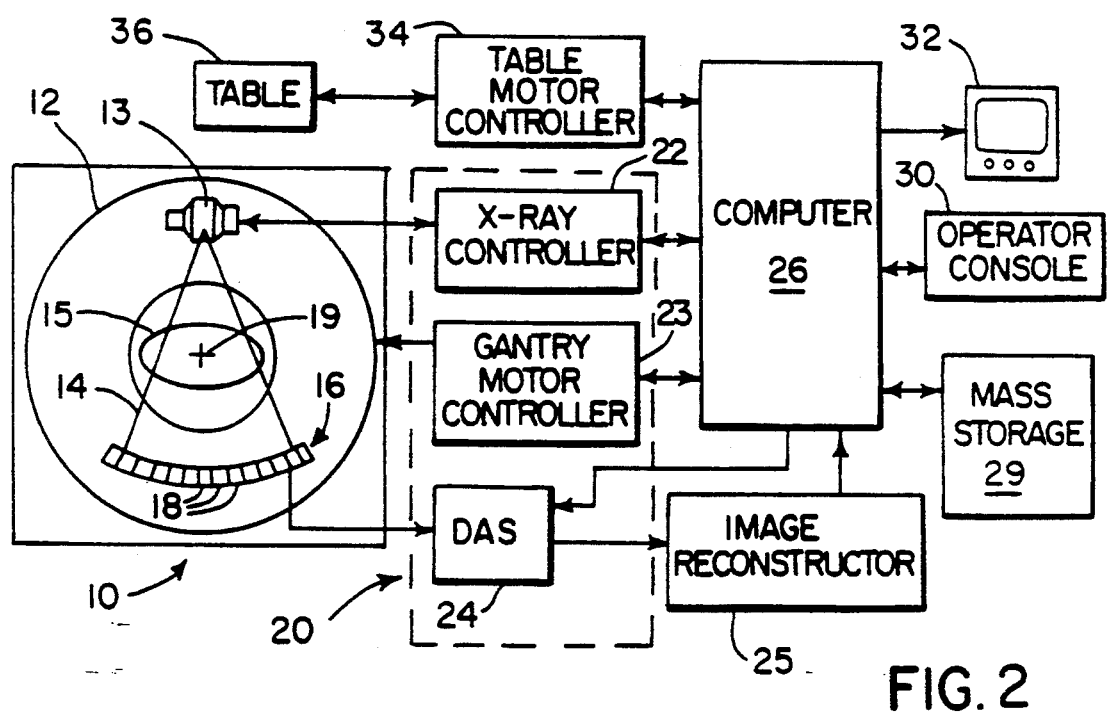
FIG. 2 is a block schematic diagram of the CT imaging system.

With initial reference to FIGS. 1 and 2, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 3A:
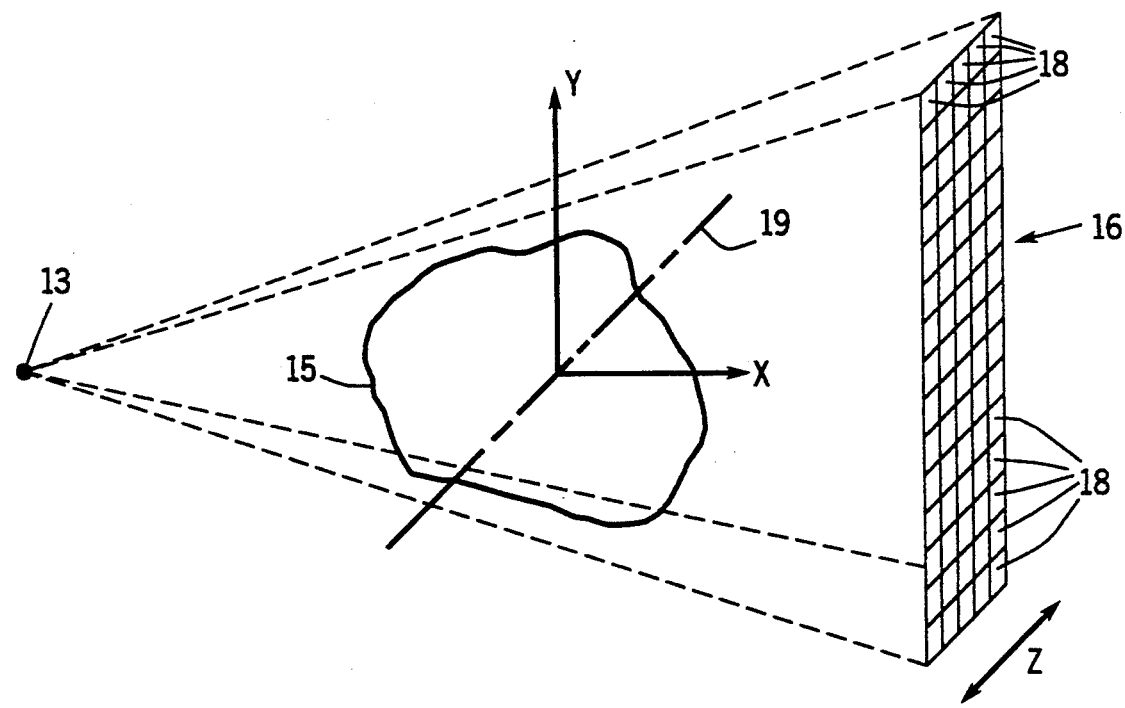
FIGS. 3a and 3b are pictorial views of the cone beam produced by the CT imaging system.
Figure 3B:
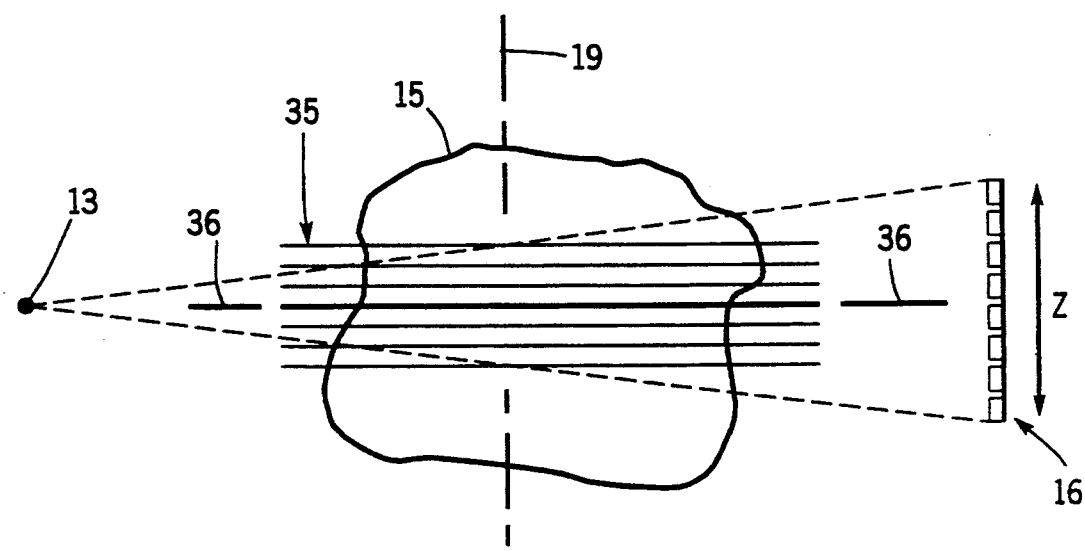

As shown best in FIG. 3a, in the preferred embodiment of the present invention the detector array 16 is a flat array of detector elements 18, having $N_r$ (e.g. 1000) elements 18 disposed along the in-plane (x,y) direction, and $N_z$ (e.g. 16) elements 18 disposed along the z axis. The x-ray beam emanates from the x-ray source 13 and fans out as it passes through the patient 15 and intercepts the detection array 16. Each acquired view is a $N_r$ by $N_z$ array of attenuation measurements as seen when the gantry is oriented in one of its positions during the scan. As shown in FIG. 3B, the object of the present invention is to reconstruct as set of 2D image slices 35 from the 3D array of acquired data produced by the x-ray cone beam during the scan. It can be seen that because the cone beam diverges as it passes through the patient 15, the reconstruction of the parallel image slices 35 is not possible with a straight forward fan beam filtering and backprojection process. The present invention enables a more accurate reconstruction of the image slices 35 from this acquired cone beam data.

Cone beam tomographic imaging uses a 2D array detector to record 2D line-projection measurements of a function to be reconstructed. Let this function be denoted as $f(\vec{r})$, where $\vec{r}$ is the position vector. Assume that the function $f(\vec{r})$ has a finite support, denoted as $\Omega$. Let $\Gamma$ denote the scanning orbit. For simplicity, assume that the 2D detecting surface forms a flat plane that contains the origin O. Actual physical detector arrangements can be converted to this form by mapping. A set of 2D projection measurements can be characterized by $P_{os}(Y,Z)$, where the vertex position of a cone beam is described by OS and each ray within the cone beam is characterized by its intersection with the detector plane, denoted as (Y,Z). Let X', Y' and Z' denote the unit vectors along SO, the Y axis and the Z axis, where the Z axis is along the axis of rotation.

Circular scanning, in theory, can not collect a complete set of data to support an exact reconstruction. In this case, the image function to be reconstructed, denoted as $f(\vec{r})$, can be split into two terms:

$$F(\vec{r}) = f_M(\vec{r}) + f_N(\vec{r}) \tag{1}$$

where $f_M(\vec{r})$ and $f_N(\vec{r})$ represent, respectively, the corresponding portion of $f(\vec{r})$ that is supported and is not supported by the projection data. In most practical applications, especially when cone angle is not large, $f_N(\vec{r})$ is small and a crude estimation of $f_N(\vec{r})$ would be sufficient. On the other hand, the image quality is primarily determined by the quality of the $f_M(\vec{r})$ reconstruction. It is highly desirable, therefore, to have a methodology for $f_M(\vec{r})$ reconstruction that is mathematically rigorous and that can also be implemented accurately and computationally efficiently on commercially available systems.

It is a discovery of the present invention that $f_M(\vec{r})$ in equation 1 can be further split into two terms:

$$f_m = f_{M0}(\vec{r}) + f_{M1}(\vec{r}) \tag{2}$$

where $f_{M0}(\vec{r})$ represents an image reconstructed using the Feldkamp method; and $f_{M1}(\vec{r})$ represents the part of $f_M(\vec{r})$ that is supported by the projection data but that is lost in the Feldkamp reconstruction method. It is further discovered and set forth in detail in Appendix A that the formula for the $f_{M1}(\vec{r})$ reconstruction can be expressed as follows:

$$f_{M1}(r) = f_{M1}(r,\psi,z) = -\frac{1}{2\pi} \int_{\phi=0}^{2\pi} d\phi \frac{z}{(d + r \cdot x')} p_{os}(Z_0) \tag{3}$$

where:

$$Z_0 = \frac{dz}{d + r \cdot x'} \tag{4}$$

$$p_{os}(Z) = \frac{1}{2\pi} \frac{\partial \sigma_{os}(Z)}{\partial Z} = \int F\sigma_{os}(\omega_z) j\omega_z e^{j2\pi\omega_z Z} d\omega_z \tag{5}$$

$$\sigma_{os}(Z) = \Sigma_{os}(l = Z, \Theta = 0) = \int P_{os}(Y,Z) dY \tag{6}$$

$$P_{os}(Y,Z) = \frac{d}{\sqrt{d^2 + Y^2 + Z^2}} P_{os}(Y,Z) \tag{7}$$

The $F\sigma_{os}(\omega_z)$ is the Fourier transform of $\sigma_{os}(Z)$.

Figure 5:
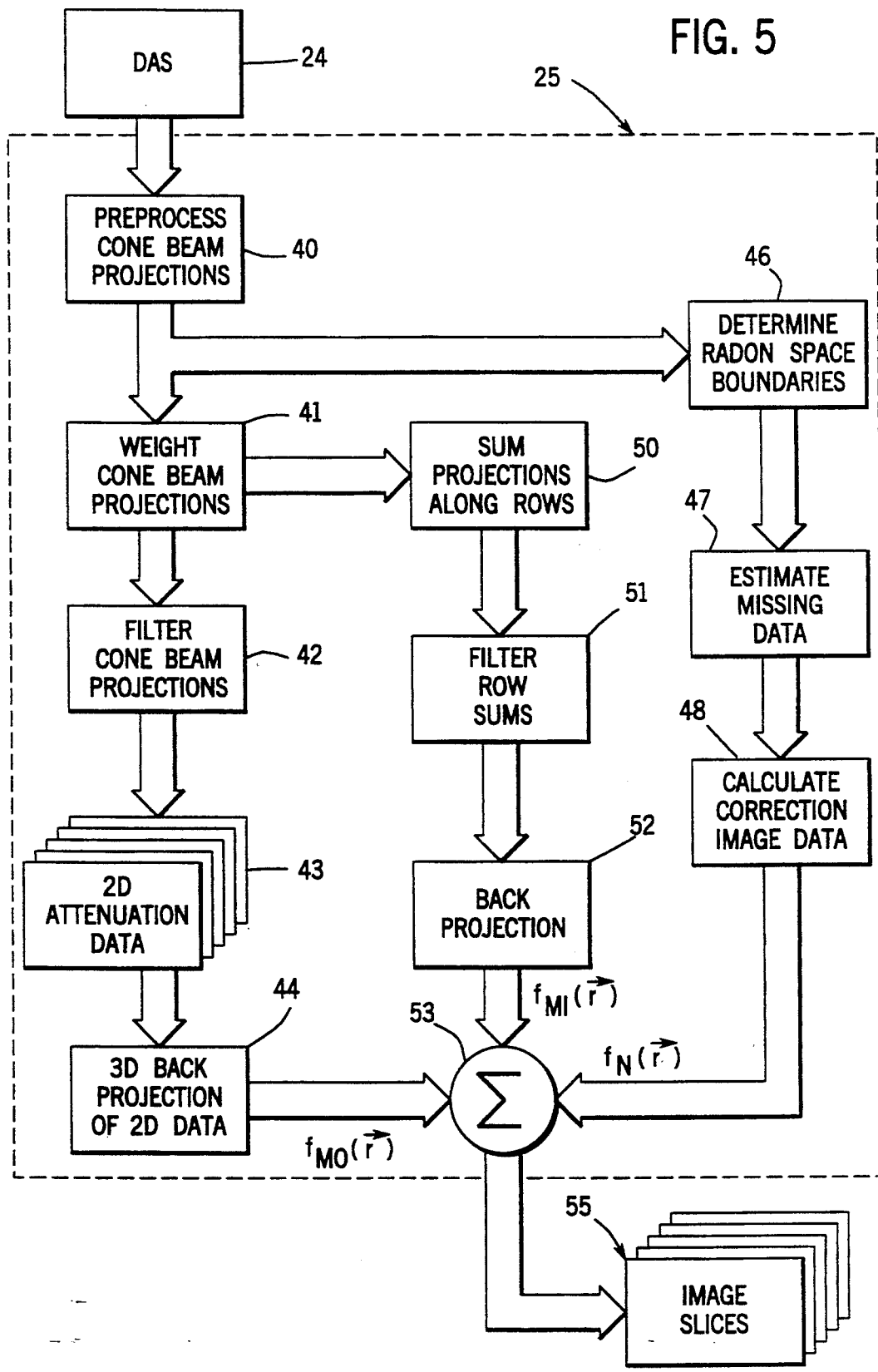
FIG. 5 is a block diagram of the image reconstructor which forms part of the CT imaging system of FIG. 2.

This reconstruction method is implemented in the image reconstructor 25. Referring particularly to FIG. 5, the cone beam projection data is received from the DAS 24 as a two-dimensional array of values which are preprocessed in the standard manner at process block 40. Such preprocessing includes correcting for known errors and offsets and calculating the minus log of the data to convert it to x-ray attenuation values.

The preprocessed cone beam attenuation profiles are used to separately calculate $f_{M0}(\vec{r})$, $f_{M1}(\vec{r})$ and $f_N(\vec{r})$. The main image term $f_{M0}(\vec{r})$ is calculated in a sequence of steps indicated by process blocks 41–44 which is essentially the method described by Feldkamp et al. It includes multiplying the cone beam projection data by weighting factors, as indicated at process block 41:

$$P_\Phi'(Y,Z) = P_\Phi(Y,Z) d / \sqrt{d^2 + Y^2 + Z^2} \tag{8}$$

where d=distance from x-ray source to detector element.

The resulting projection data is then filtered by convolving it with a filter kernal as indicated at process block 42.

$$P_\Phi(Y,Z) = \int_{-\infty}^{\infty} dY' \int_{-\infty}^{\infty} dZ' g_y(Y - Y') g_z(Z - Z') P_\Phi'(Y',Z') \tag{9}$$

where the kernals are:

$$g_y(Y) = Re \int_0^{\omega_{y0}} \omega d\omega e^{i\omega y}$$

$$g_z(Z) = \sin\omega_{z0}Z/\pi Z$$

The filtered attenuation data is then back projected from each detector element position back along the ray extending from the point source of the x-ray cone beam. This results in a 3D image array $f_{M0}(\vec{r})$.

$$f_{M0}(r) = \frac{1}{4\pi^2} \int d\Phi \frac{d^2}{(d + r \cdot x')^2} P_\Phi[Y(r), Z(r)] \quad (10)$$

where $$Y(\vec{r}) = \vec{r} \cdot Y d/(d + \vec{r} \cdot X')$$

$$Z(\vec{r}) = \vec{r} \cdot Z d/(d + \vec{r} \cdot X')$$

As is well known in the art, the image reconstructed in this manner through the midplane of the cone beam is very accurate. However, as the images move away from this midplane image, their quality decreases due to errors in the methodology and incomplete data. Corrections for this deterioration in image quality is provided by the $f_{M1}(\vec{r})$ and $f_N(\vec{r})$ image terms described above and calculated as will now be described.

Referring still to FIG. 5, the correction image $f_{M1}(\vec{r})$ is derived from the weighted cone beam projections produced at process block 41 and indicated above in equation (7). This two-dimensional weighted cone beam projection $P_{OS}(Y,Z)$ is then summed along the row direction (Y) at process block 50 to produce the one-dimensional row sum $\sigma_{OS}(Z)$ indicated above in equation (6). This is filtered at process block 51 by a one-dimensional filter $(j\omega_z)$, as indicated above in equation (5) to produce the filtered row sum $p(z)$. This filtering can also be performed by directly differentiating the row sum $\sigma_{OS}(Z)$, also as shown in equation (5). The filtered row sum for every projection in the scan is then weighted by a position-dependent factor and the resulting data is back projected at process block 52 in accordance with the above equation (3) to produce the correction image $f_{M1}(\vec{r})$.

The third term $f_N(\vec{r})$ may be estimated using a number of known methods, but a methodology disclosed in the above-cited Grangeat publication is presently preferred and is incorporated herein by reference. More specifically, Radon set S can be divided into two subsets, subset D which is supported by projection data, and subset C that is not supported by projection data. Next, $\partial Rf/\partial \rho$ on the boundary of subset D is calculated from the cone beam projection data using the following equation disclosed by Grangeat that relates the derivative of cone beam plane integral to the derivative of parallel beam plane integral:

$$\frac{\partial Rf}{\partial \rho} (OS \cdot n, n) = \frac{|OS|^2}{|OS \times n|^2} \frac{\partial \Sigma_{os}(1,\Theta)}{\partial l} \quad (11)$$

where, the line denoted by $(1,\theta)$ is the intersection of the plane P characterized by $(\rho = OS \cdot \vec{n}, \vec{n})$ and the detector plane denoted by OS. Next $\partial Rf/\partial \rho$ is estimated in subset C. Note that since subset C is not supported by cone beam projection data, we assume that $\partial Rf/\partial \rho$ is continuous at the boundary of subset D and C, and interpolate therebetween. Having calculated these values, $f_N(\vec{r})$ may be calculated as follows:

$$f_N(r) = -\frac{1}{8\pi^2} \int \int_C \frac{\partial R^2 f}{\partial \rho^2} (\rho,n) \delta(r \cdot n - \rho) d\rho \, dn \quad (12)$$

Referring to FIG. 5, to produce the corrective image $f_N(\vec{r})$ the acquired and preprocessed cone beam attenuation data is applied to a process block 46 in calculated as set forth above in equation (11). As indicated at process block 47, the data values in subset C are then calculated by interpolating between values at the boundaries with subset D, and these estimated values are applied to process block 48 which calculates the correction images $f_N(\vec{r})$ using the above equation (12). The corresponding slices in each image $f_{M0}(\vec{r})$, $f_{M1}(\vec{r})$ and $f_N(\vec{r})$ are added together at summing point 53 to produce the final image slices 55 for the computer 26.

APPENDIX A

Figure 4:
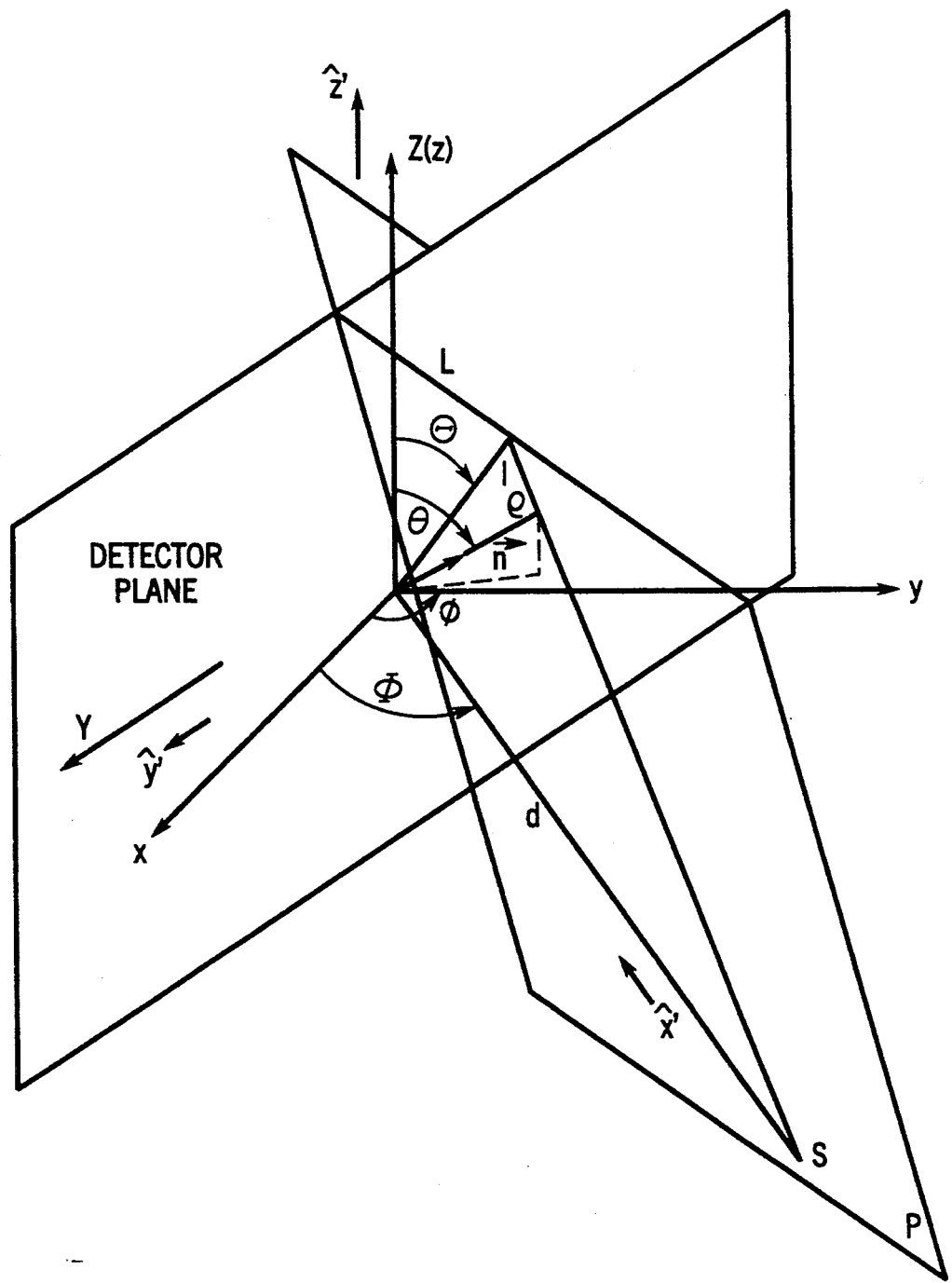
FIG. 4 is a graphic illustration of the coordinate systems used to define the reconstruction process.

In the following discussion reference is made to the coordinate system and system geometry shown in FIG. 4. The circular scanning orbit, though incapable of collecting a complete set of data, is of great practical and theoretical interests due to the simplicity and the symmetry it offers. Consider a circular scanning orbit of radius d. In this case, OS can be described as:

$$OS = (d \cos \phi, \sin \phi, 0) \quad (A1)$$

Note that now the detector coordinates (1, $\Theta$, OS) can also be characterized as (1, $\theta$, $\phi$).

For a circular scan, set $S(\Gamma)$ forms a torus described by the relation: $\rho < d \sin \theta$, and the image $f_M(\vec{r})$ terms can be expressed in $(\rho, \theta, \phi)$ as:

$$f_{M0}(r) = \frac{1}{8\pi^2} \int_{\phi=0}^{2\pi} \int_{\theta=0}^{\pi} \int_{\rho=-d\sin\theta}^{\pi} \frac{\partial Rf}{\partial \rho}(\rho,n) \quad (A2)$$
$$\frac{\partial \delta}{\partial \rho}(r \cdot n - \rho) \sin\theta \, d\rho \, d\theta \, d\phi$$

and $$f_{M1}(r) = -\frac{1}{8\pi^2} \int_{\phi=0}^{2\pi} \int_{\theta=0}^{\pi} d\theta \, d\phi \sin\theta \quad (A3)$$
$$\frac{\partial Rf}{\partial \rho}(\rho,n) \delta(r \cdot n - \rho)|_{\rho=-d\sin\theta}^{\rho=d\sin\theta}$$

What follows is a proof that $f_{M0}(\vec{r})$ is equivalent to the Feldkamp image reconstruction. In set $S(\Gamma)$, $(\rho, \theta, \phi)$ and $(1, \theta, \Phi)$ have the following relations:

$$l = \frac{d\rho}{\sqrt{d^2 - \rho^2}} \quad (A4)$$

$$\Theta = \arccos\left(\frac{d}{\sqrt{d^2 - \rho^2}} \cos\theta\right) \quad (A5)$$

$$\Phi = \phi + \arccos\left(\frac{\rho}{d \sin\theta}\right) \quad (A6)$$

Therefore, the Jacobean for the transformation from $(\rho, \theta, \phi)$ and $(1, \theta, \phi)$ is $$J = \frac{\sin\Theta}{\sin\theta} \frac{d^4}{(d^2 + l^2)^2} \tag{A7}$$

One then has:

$$\frac{\partial Rf}{\partial \rho}(OS \cdot n, n) = \frac{d^2 + l^2}{d^2} \int FP_{os}(\omega,\Theta)j2\pi\omega e^{j2\pi\omega l}d\omega \tag{A8}$$

Furthermore, the derivative of the delta function in Equation (A2) can be rewritten as follows:

$$\frac{\partial\delta}{\partial\rho}(r \cdot n - \rho) = \frac{d^2 + l^2}{d^2} \frac{d^2}{(d + r \cdot x')^2} \tag{A9}$$
$$\frac{\partial\delta}{\partial l}(Y_0\sin\Theta + Z_0\cos\Theta - l)$$

where $$Y_0 = \frac{dr \cdot y'}{d + r \cdot x'} \quad Z_0 = \frac{dz}{d + r \cdot x'}$$

Using Equations (A7), (A8) and (A9), Equation (A2) can be rewritten in $(l, \theta, \Phi)$ coordinate system as:

$$f_{M0}(r) = \frac{1}{8\pi^2} \int d\Phi \frac{d^2}{(d + r \cdot x')^2} \int_{\Theta=0}^{\pi} d\Theta \sin\Theta \tag{A10}$$
$$\int_{l=-\infty}^{\infty} dl \frac{\partial\delta}{\partial l}(Y_0\sin\Theta + Z_0\cos\Theta - l)$$
$$\int FP_{os}(\omega,\Theta)j2\pi\omega\, e^{j2\pi\omega l}d\omega$$

Using the property of delta function, Equation (A10) can further be reduced to:

$$f_{M0}(r) = \frac{1}{2}\int d\Phi \frac{d^2}{(d + r \cdot x')^2} \int_0^\pi \int FP_{os} \tag{A11}$$
$$(\omega,\Theta)\omega^2 \sin\Theta e^{j2\pi\omega(Y_0\sin\Theta + Z_0\cos\Theta)} d\omega d\Theta$$

By examining equation (A11) one can conclude that $f_{M0}(\vec{r})$ is equivalent to the Feldkamp method. In addition, using the property of delta function, equation (A3) can be simplified as follows:

$$f_{M1}(r) = f_{M1}(r,\psi,z) = -\frac{1}{8\pi^2}\int_{\phi=0}^{2\pi} d\phi \tag{A12}$$
$$(L_+(r,\psi,z,\phi) - L_-(r,\psi,z,\phi))$$

where $$L_\pm(r,\psi,z,\phi) = \frac{|z|}{H_\pm^2} \frac{\partial RF}{\partial\rho}\left(\pm\frac{d|z|}{H_\pm}, \arctan \frac{z}{\pm d - r\cos(\phi - \psi)}, \phi\right) \tag{A13}$$

and $$H_\pm(\phi,r,\psi,z) = \sqrt{[r\cos(\phi - \psi) - \pm d]^2 + z^2} \tag{A14}$$

Transforming from the spherical coordinate system $(\rho, \theta, \phi)$ to the detector coordinate system $(l, \Theta, \Phi)$, one has:

$$f_{M1}(r) = f_{M1}(r,\psi,z) = -\frac{1}{2\pi}\int_{\phi=0}^{2\pi} d\phi \frac{z}{(d + r \cdot x')} p(Z_0) \tag{3}$$

where:

$$Z_0 = \frac{dz}{d + r \cdot x'} \tag{4}$$

$$p(Z) = \frac{1}{2\pi}\frac{\partial\sigma_{os}(Z)}{\partial Z} = \int F\sigma_{os}(\omega_z)j\omega_z e^{j2\pi\omega_z Z} d\omega_z \tag{5}$$

$$\sigma_{os}(Z) = \Sigma_{os}(l = Z, \Theta = 0) = \int P_{os}(Y,Z)dY \tag{6}$$

The $F\sigma_{os}(\omega_z)$ is the Fourier transform of $\sigma_{os}(Z)$.

I claim:

1. A computed tomography imaging system which comprises:
   a two-dimensional array of detector elements for receiving photons emanating in a cone beam from a source;
   a digital acquisition system for acquiring two-dimensional arrays of cone beam data from the array of detector elements at a series of views in which the array of detector elements revolves around a central axis;
   a filter for receiving the cone beam data and filtering the same;
   means for back projecting the filtered cone beam data to produce image data $f_{M0}(\vec{r})$;
   row summing means for receiving the cone beam data and summing the values therein along one of two dimensions of said two-dimensional arrays of cone beam data to form one-dimensional arrays of row sum data;
   means for filtering the row sum data;
   means for back projecting the filtered row sum data to produce corrective image data $f_{M1}(\vec{r})$; and
   summing means for combining the image data $f_{M0}(\vec{r})$ with the correction image data $f_{M1}(\vec{r})$ to produce an image slice.

2. The computed tomography system as recited in claim 1 which includes:
   means for receiving the cone beam data and estimating values not provided by the received cone beam data;
   means for receiving the estimated values and calculating corrected image data $f_N(\vec{r})$; and
   the summing means also combines the corrected image data $f_N(\vec{r})$ to produce the image slice.

3. The system as recited in claim 1 which includes means for weighting the cone beam data prior to its application to the filter and the row summing means.

4. The system as recited in claim 1 in which the source produces x-rays and is located on the side opposite the array of detector elements from the central axis, and both the array of detector elements and x-ray source are revolved around the central axis during the acquisition of said series of views.

5. The system as recited in claim 4 in which the acquired cone beam data is preprocessed to provide x-ray attenuation data for a three-dimensional region about the central axis and between the x-ray source and the array of detector elements, and the image data $f_{M0}(\vec{r})$ and corrective image data $f_{M1}(\vec{r})$ is summed to produce a plurality of two-dimensional image slices through said three-dimensional region.

* * * * *